United States Patent [19]

Lewis et al.

[11] 4,235,620
[45] Nov. 25, 1980

[54] AZOLYL-SUBSTITUTED UNSATURATED KETONES AND HERBICIDAL USE THEREOF

[75] Inventors: Terence Lewis, Bracknell; Sugavanam Balasubramanyan, Wokingham, both of England

[73] Assignee: Imperial Chemical Industries Limited, London, England

[21] Appl. No.: 825,784

[22] Filed: Aug. 18, 1977

[30] Foreign Application Priority Data

Aug. 27, 1976 [GB] United Kingdom ............... 35736/76

[51] Int. Cl.$^2$ ...................... A01N 9/22; C07D 249/08
[52] U.S. Cl. ......................................... 71/92; 542/429;
542/431; 542/436; 542/440; 548/101; 548/262; 548/341
[58] Field of Search ............... 542/429, 436, 440, 431; 548/341, 101, 262; 260/308 R, 299; 71/92

[56] References Cited

U.S. PATENT DOCUMENTS

| | | | |
|---|---|---|---|
| 3,398,144 | 8/1968 | Laliberte et al. | 542/938 |
| 3,753,983 | 8/1973 | Raabe et al. | 542/440 |
| 4,038,406 | 7/1977 | Meiser et al. | 424/269 |
| 4,067,989 | 1/1978 | Shephard et al. | 424/273 R |
| 4,079,143 | 3/1978 | Balasubramanyan et al. | 260/308 R |
| 4,086,351 | 4/1978 | Balasubramanyan et al. | 260/308 R |

OTHER PUBLICATIONS

Smith, Open–Chain Nitrogen Compounds, vol. 1, (W. A. Benjamin, Inc., New York, 1965), p. 331.

*Primary Examiner*—Alton D. Rollins
*Attorney, Agent, or Firm*—Cushman, Darby & Cushman

[57] ABSTRACT

Herbicidal compounds of the formula

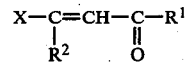

wherein X is a 1(1,2,4-triazolyl)radical or a 1-imidazolyl radical and $R^1$ and $R^2$ are alkyl or cycloalkyl radicals of 2 to 10 carbon atoms or phenyl or naphthyl radicals optionally bearing specified substituents, and acid addition salts and metal complexes thereof. These compounds are useful as general herbicides and as selective herbicides in maize, rice, soya, sorghum and oil-seed rape.

8 Claims, No Drawings

AZOLYL-SUBSTITUTED UNSATURATED KETONES AND HERBICIDAL USE THEREOF

This invention relates to chemical compounds having herbicidal properties, and to herbicidal processes and compositions utilising these compounds.

According to the present invention there are provided herbicidal compounds of the formula:-

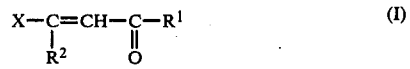   (I)

wherein X is a 1-(1,2,4-triazolyl) radical or a 1-imidazolyl radical; $R^2$ is an alkyl or cycloalkyl radical of 2 to 10 carbon atoms or a phenyl or naphthyl radical optionally bearing one or more of the following substituents: fluorine; chlorine; bromine; iodine; cyano; nitro; alkyl of 1 to 6 carbon atoms; alkoxy of 1 to 6 carbon atoms optionally substituted by one or more phenyl radicals or alkoxy radicals of 1 to 6 carbon atoms; alkylthio of 1 to 6 carbon atoms; haloalkyl of 1 to 6 carbon atoms; haloalkoxy of 1 to 6 carbon atoms; carboxyalkoxy in which the alkoxy group has from 1 to 6 carbon atoms; alkoxycarbonylalkoxy in which each alkoxy group has from 1 to 6 carbon atoms; N,N-dialkylcarbamoylalkoxy in which the alkoxy group and each alkyl group each has from 1 to 6 carbon atoms; phenyl; or 1-(1,2,4-triazolyl)vinyl; and $R^1$ is an alkyl or cycloalkyl radical of 2 to 10 carbon atoms, or a phenyl or naphthyl radical optionally bearing one or more of the substituents listed for $R^2$ above; or an acid addition salt or metal complex thereof.

The identity of the acid which is used to form the acid addition salts of the compounds of the invention is not critical and a wide variety of acid addition salts of any particular compound may therefore be used. For reasons of convenience and economy, however, salts derived from the readily available mineral acids are preferred, although others may be used if desired. In considering the choice of acid, the purpose for which the salt is to be used will be taken into account; salts formed from herbicidal acids which are highly persistent in soil would obviously not be suitable for applications in which crops are to be planted shortly after the herbicide is applied. Particular examples of acids which may be used to form the acid addition salts include hydrochloric, hydrobromic, sulphuric, nitric, phosphoric, and p-toluene sulphonic acids.

The compounds of the invention form complexes with salts of transition metals, for example copper and zinc salts, and such complexes form part of the invention. Conveniently the transition metal salts are halides, sulphates or nitrates. The metal complexes usually contain two molar proportions of the compound of the invention to one molar proportion of the metal salt. They may be prepared by mixing solutions of the compound and the metal salt and collecting the precipitated complex. The solvent may be for example a lower alkanol, for example methanol or ethanol.

Sub-groups of compounds falling within the broad class of compounds defined above include the group in which $R^1$ is a tertiary butyl radical, X is a 1(1,2,4-triazolyl) or 1-imidazolyl radical, and $R^2$ is a substituted phenyl or naphthyl radical. When $R^2$ is a substituted phenyl radical, it is usually the case that the most active compounds are those in which the 4-position of the phenyl ring is left free and the substituents are located in one or more of the 2, 3, 5 or 6-positions of the phenyl ring. In disubstituted compounds it is preferred to have the substituents in the 2,5 or 2,6-positions of the phenyl ring. Preferred compounds include those in which $R^2$ is a phenyl group substituted with an alkoxy group in the 2-position and a halogen atom in the 5-position, for example 2-ethoxy-5-bromophenyl and 2-ethoxy-5-chlorophenyl. When $R^2$ is a 1-naphthyl radical, there is no preference for keeping the 4-position free and this position may be substituted with, for example, an alkoxy group, for example a methoxy group.

A further subgroup of compounds within the broad class of compounds according to the invention includes those compounds in which X is a 1(1,2,4-triazolyl) group or a 1-imidazolyl group, $R^1$ is a phenyl group optionally bearing one or more of the following substituents: fluorine, chlorine, bromine, iodine, alkyl of 1 to 6 carbon atoms, alkoxy of 1 to 6 carbon atoms optionally substituted with one or more phenyl radicals, or haloalkyl of 1 to 6 carbon atoms and $R^2$ is a phenyl radical bearing any of the substituents listed for $R^2$ above.

When $R^1$ or $R^2$ is an alkyl radical, it may be a straight chain or branched alkyl radical, for example an alkyl radical of up to 6 carbon atoms, or a cycloalkyl radical, for example a cyclopropyl, cyclopentyl, or cyclohexyl radical.

The compounds of the invention are capable of existing in two geometrically isomeric forms (cis and trans), according to the disposition of the groups attached to the carbon atoms linked by a double bond. Both isomers, and mixtures thereof, form part of the invention. Generally in a given preparation one isomer is produced in greater proportion than the other. If desired, the isomers can be separated by conventional chemical methods, for example by gas-liquid chromatography (GLC). It may be more convenient, however, to use the mixture of isomers as a herbicide. The proportion of each isomer in the mixture may readily be determined by physical methods of analysis, for example by examination of the nuclear magnetic resonance spectrum of the product since the spectra of the two isomers differ from each other. The two isomers of a given compound may not be completely identical in biological activity in every case.

Particular examples of compounds according to the invention are listed in Table I.

TABLE I $$X-C(R^2)=CH-C(=O)-R^1$$

| COMPOUND NO | X | $R^1$ | $R^2$ | MELTING POINT °C. |
|---|---|---|---|---|
| 1 | T | t Bu | Ph | 70–73 |
| 2 | T | t Bu | o Cl . $C_6H_4$ | 53–55 |
| 3 | T | Ph | o Cl . $C_6H_4$ | 79–81 |
| 4 | Im | Ph | o Cl . $C_6H_4$ | 128 |
| 5 | Im | t Bu | o Cl . $C_6H_4$ | 74 |

TABLE I-continued $$X-\underset{R^2}{\underset{|}{C}}=CH-\underset{O}{\underset{\|}{C}}-R^1$$

| COMPOUND NO | X | R¹ | R² | MELTING POINT °C. |
|---|---|---|---|---|
| 6 | T | t Bu | o CH₃O . C₆H₄ | 95.5–96.5 |
| 7 | Im | t Bu | o CH₃O . C₆H₄ | 122 |
| 8 | Im | t Bu | o EtO . C₆H₄ | 98 |
| 9 | T | t Bu | o EtO . C₆H₄ | 72–75 |
| 10 | T | t Bu | o Me . C₆H₄ | oil |
| 11 | T | p Meo . C₆H₄ | o Cl . C₆H₄ | PTS 151–153 |
| 12 | T | iso Pr | o Cl . C₆H₄ | oil |
| 13 | T | cyclohexyl | o Cl . C₆H₄ | oil |
| 14 | Im | p MeO . C₆H₄ | o Cl . C₆H₄ | 84–87 |
| 15 | T | p-F . C₆H₄ | o Cl . C₆H₄ | PTS 153–154 |
| 16 | T | t Bu | o F . C₆H₄ | PTS 174–175 |
| 17 | T | Ph | Ph | 153–155 |
| 18 | T | Ph | o MeO . C₆H₄ | 93–94 |
| 19 | T | t Bu | m CF₃ . C₆H₄ | PTS 183–186 |
| 20 | T | iso Pr | Ph | PTS 175–177 |
| 21 | T | t Bu | m Cl . C₆H₄ | PTS 173–175 |
| 22 | T | t Bu | 2,4-Cl₂ . C₆H₄ | PTS 154–155 |
| 23 | Im | t Bu | 2,4-Cl₂ . C₆H₄ | 112–114 |
| 24 | Im | t Bu | m Cl . C₆H₄ | PTS 200–202 |
| 25 | T | Ph | o Me . C₆H₄ | PTS 124–125 |
| 26 | T | Ph | o F . C₆H₄ | PTS 166–168 |
| 27 | T | p F . C₆H₄ | o MeO . C₆H₄ | 124–125 |
| 28 | T | t Bu | 2,6-Cl₂ . C₆H₃ | 104–105 |
| 29 | T | Ph | Ph | 140–142 |
| 30 | T | p MeO . C₆H₄ | o MeO . C₆H₄ | PTS 150–155 |
| 31 | T | Ph | p-CN . C₆H₄ | PTS 181–182 |
| 32 | T | o Cl . C₆H₄ | Ph | PTS 172–173 |
| 33 | T | o MeO . C₆H₄ | o Cl . C₆H₄ | 87–89 |
| 34 | T | o MeO . C₆H₄ | o Cl . C₆H₄ | PTS 126–128 |
| 35 | T | t Bu | 2 EtO-5-Br . C₆H₃ | 121–125 |
| 36 | T | t Bu | o EtO . C₆H₄ | 95–97 |
| 37 | T | t Bu | o Br . C₆H₄ | PTS 128–130 |
| 38 | T | t Bu | 2,5-Me₂ . C₆H₃ | 77–78 |
| 39 | T | t Bu | p MeO . C₆H₄ | PTS 165–166 |
| 40 | T | t Bu | 1-naphthyl | 81 then 103–104 |
| 41 | T | t Bu | m Cl . C₆H₄ | 173–175 |
| 42 | T | t Bu | m CF₃C₆H₄ | 60–62 |
| 43 | Im | t Bu | m Cl . C₆H₄ | 75–78 |
| 44 | T | t Bu | m CN . C₆H₄ | oil |
| 45 | T | t Bu | 2-Cl-6-F . C₆H₃ | 75–80 |
| 46 | Im | t Bu | 2,3-(MeO)₂C₆H₃ | 56–58 |
| 47 | Im | t Bu | o Br . C₆H₄ | 73–74 |
| 48 | Im | t Bu | o MeO . C₆H₄ | 118–120 |
| 49 | Im | o Meo . C₆H₄ | o Cl . C₆H₄ | 65–68 |
| 50 | Im | t Bu | Ph | 67–68 |
| 51 | T | t Bu | 2-MeO-5-Br-C₆H₃ | 126–127 |
| 52 | T | t Bu | 2,3-(MeO)₂ . C₆H₃ | 68–70 |
| 53 | T | t Bu | 2-EtO-3-MeO-C₆H₃ | oil |
| 54 | Im | t Bu | 2-Cl-6-F . C₆H₃ | PTS 155–157 |
| 55 | Im | t Bu | 2-MeO-5-Br . C₆H₃ | 122–124 |
| 56 | Im | t Bu | m MeO . C₆H₄ | oil |
| 57 | Im | t Bu | o Me . C₆H₄ | 87–88 |
| 58 | T | t Bu | m MeO . C₆H₄ | oil |
| 59 | T | t Bu | 2-Br-4,5-(MeO)₂ . C₆H₂ | 117 |
| 60 | Im | t Bu | 2,6-Cl₂C₆H₄ | 100–104 |
| 61 | T | Me | o-Cl . C₆H₄ | oil |
| 62 | T | t Bu | m . EtO . C₆H₄ | 57–58 |
| 63 | T | t Bu | p-Cl . C₆H₄ | 100–114 |
| 64 | T | Ph | iso Pr | $n_D^{24}$ 1.553 |
| 65 | T | t Bu | 3-pentyl | b.p. 112° C./0.05 Torr |
| 66 | T | t Bu | 2,5-(MeO)₂ . C₆H₃ | 98 |
| 67 | Im | t Bu | 1-naphthyl | 133–135 |
| 68 | T | t Bu | 2-naphthyl | 80–83 then 95–101 |
| 69 | Im | t Bu | 2-naphthyl | 91–100 |
| 70 | T | t Bu | 3,4-(MeO)₂ . C₆H₃ | oil |
| 71 | Im | t Bu | 3,4-(MeO)₂ . C₆H₃ | oil |
| 72 | Im | t Bu | m-Me . C₆H₄ | 78 |
| 73 | T | t Bu | 4-MeO-1-naphthyl | 143–148 |
| 74 | T | t Bu | 2-PhCH₂O . C₆H₄ | oil |

TABLE I-continued $$X-\underset{R^2}{\underset{|}{C}}=CH-\underset{O}{\underset{\|}{C}}-R^1$$

| COMPOUND NO | X | R¹ | R² | MELTING POINT °C. |
|---|---|---|---|---|
| 75 | T | t Bu | 2-PrO-3-MeO . C₆H₃ | oil |
| 76 | T | adamantyl | 2-MeO . C₆H₄ | 136 |
| 77 | T | t Bu | 3-Me . C₆H₄ | 48 |
| 78 | T | t Bu | 2-PhCH₂O-5-MeO . C₆H₃ | 100 |
| 79 | T | t Bu | 2-iso PrO-3-MeO C₆H₃ | oil |
| 80 | T | t Bu | 2-iso PrO-5-MeO . C₆H₃ | oil |
| 81 | T | t Bu | 2-MeO-6-Cl . C₆H₃ | oil |
| 82 | Im | t Bu | 2,4,6-Me₃ . C₆H₂ | 81–83 |
| 83 | Im | t Bu | 2-MeO-6-Cl . C₆H₃ | oil |
| 84 | T | t Bu | 2-PrO . C₆H₄ | oil |
| 85 | Im | t Bu | 2-PrO . C₆H₄ | 67–69 |
| 86 | Im | t Bu | 2-iso PrO-3-MeO . C₆H₃ | 92 |
| 87 | Im | t Bu | 2-iso PrO-3-MeO . C₆H₃ | oil |
| 88 | Im | t Bu | 2-EtO-3-Meo . C₆H₃ | oil |
| 89 | T | t Bu | 2-NO₂ . C₆H₄ | 118–120 |
| 90 | T | t Bu | 3-Br . C₆H₄ | 87–89 |
| 91 | T | Bu | 2-Cl . C₆H₄ | oil |
| 92 | T | t Bu | 2,6-Me₂C₆H₃ | 72–80 |
| 93 | T | t Bu | 2-MeO-1-naphthyl | 150–152 |
| 94 | Im | t Bu | 2,6-Me₂ . C₆H₃ | 102–103 |
| 95 | T | t Bu | 2-Br-5-MeO . C₆H₃ | 112–114 |
| 96 | T | t Bu | 2-CF₃ . C₆H₄ | 65–67 |
| 97 | T | t Bu | 2-iso PrO-5-Br . C₆H₃ | 118–119 |
| 98 | Im | t Bu | 2-CF₃ . C₆H₄ | 91–93 |
| 99 | T | t Bu | o-HCO₂CH₂O . C₆H₄ | 157–159 |
| 100 | Im | t Bu | 2-iso PrO . C₆H₄ | 83–85 |
| 101 | T | t Bu | 4-EtO-3-MeO . C₆H₃ | oil |
| 102 | Im | t Bu | 2-MeO-1-naphthyl | 88–96 |
| 103 | T | t Bu | 2-Cl-5-EtO . C₆H₃ | 91–92 |
| 104 | Im | t Bu | 2-iso BuO . C₆H₄ | 73–75 |
| 105 | T | t Bu | 2-iso PrO . C₆H₄ | 62–63 |
| 106 | T | t Bu | 2-Me₂NCCH₂O . C₆H₄ $\underset{O}{\overset{\|}{}}$ | 121–122 |
| 107 | T | t Bu | 2-CHF₂CF₂O . C₆H₄ | oil |
| 108 | Im | t Bu | 2,4-Me₂ . C₆H₃ | 78 |
| 109 | T | t Bu | 2-isoPr . C₆H₄ | oil |
| 110 | Im | t Bu | 2-iso Pr . C₆H₄ | oil |
| 111 | T | t Bu | 2,3-Me₂ . C₆H₃ | oil |
| 112 | Im | t Bu | 2,3-Me₂ . C₆H₃ | 88–90 |
| 113 | T | t Bu | 5-Cl-2-Me . C₆H₃ | 114–115 |
| 114 | Im | t Bu | 5-Cl-2-Me . C₆H₃ | 109–110 |
| 115 | Im | t Bu | 5-Cl-2-EtO . C₆H₃ | 97–99 |
| 116 | T | t Bu | 5-Cl-2-MeO . C₆H₃ | 125–126 |
| 117 | T | t Bu | 2-Cl-5-MeO . C₆H₃ | 65–67 |
| 118 | T | t Bu | 3-CHF₂CF₂O . C₆H₄ | oil |
| 119 | T | t Bu | 2-HexO-5-MeO . C₆H₃ | oil |
| 120 | T | t Bu | 2,3,4-(MeO)₃ . C₆H₂ | 117–118 |
| 121 | T | t Bu | 2,4-Me₂ . C₆H₃ | oil |
| 122 | T | t Bu | 2-Ph . C₆H₄ | 137–139 |
| 123 | I | t Bu | 2-Ph . C₆H₄ | 93–95 |
| 124 | T | t Bu | 2-EtOCH₂CH₂O . C₆H₄ | oil |
| 125 | T | t Bu | 2-(T-CH=CH) . C₆H₄ | 129–132 |
| 126 | T | t Bu | 2-MeO-3,5-Cl₂ . C₆H₂ | oil |
| 127 | Im | t Bu | 2,3,4-(MeO)₃ . | oil |

TABLE I-continued $$X-\underset{\underset{R^2}{|}}{C}=CH-\underset{\underset{O}{\|}}{C}-R^1$$

| COMPOUND NO | X | R¹ | R² | MELTING POINT °C. |
|---|---|---|---|---|
| 128 | T | t Bu | 5-Br-2-EtO-3-MeO . C₆H₂ | oil |
| 129 | T | cyclo propyl | 2-MeO . C₆H₄ | oil |
| 130 | T | t Bu | 2-MeS . C₆H₄ | 85–86 |
| 131 | T | t Bu | 3,5-Br₂-2-MeO . C₆H₂ | oil |
| 132 | Im | t Bu | Ph | PTS 194–196 |
| 133 | T | t Bu | 2-Et . C₆H₄ | oil |
| 134 | Im | t Bu | 2-Et . C₆H₄ | 95–96 |
| 135 | T | t Bu | 2-MeO . CO . CH₂O . C₆H₄ | 89–91 |
| 136 | T | t Bu | 2-EtO . COCH₂O . C₆H₄ | 82–84 |
| 137 | T | t Bu | 2-iso BuO-5-Br . C₆H₃ | 99–102 |
| 138 | T | t Bu | 2-iso BuO | oil |
| 139 | T | t Bu | 2-Br-5-EtO . C₆H₃ | 86–88 |
| 140 | T | t Bu | 2-EtO-5-Cl . C₆H₃ | 114–116 |

The following list gives the meanings of certain symbols used in Table I.

| Im | 1-imidazolyl |
|---|---|
| T | 1-(1,2,4-triazolyl) |
| Me | methyl |
| Et | ethyl |
| Pr | propyl |
| Bu | butyl |
| Hex | hexyl |
| Ph | phenyl |
| PTS | p-toluene sulphonate |

In the column of melting points given in Table I, a figure preceded by the letters PTS means that the melting point given is that of the p-toluene sulphonate salt of the compound.

Compounds no 9 and 36 of Table I are a pair of cis and trans isomers. This is also the case with compounds 17 and 29.

In another aspect the invention provides a process of killing or severely injuring unwanted plants, which comprises applying to the plants, or to the growth medium thereof, a compound of the formula:

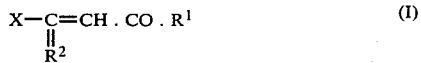

wherein X, R¹ and R² are as hereinbefore defined.

As will be appreciated by those skilled in the art, the amount of the compound (I) applied will depend on a variety of factors, for example the particular compound chosen for use and the identity of the unwanted plants. By way of general guidance, however, a rate of from 0.25 to 10 kilograms per hectare is usually suitable, while from 0.5 to 5 kilograms per hectare is preferred.

Many of the compounds of the invention are broad-spectrum herbicides; that is to say, they are toxic towards a wide variety of plant species. A valuable feature of the compounds of the invention is that they are often effective in the control of the weed *Cyperus rotundus*, a species which is difficult to control with previously known herbicides. Examples of compounds effective against *Cyperus rotondus* include compounds no 6 and 9 of Table I.

Certain compounds of the invention are relatively less toxic towards particular crop plants and may be used as selective herbicides to inhibit the growth of weeds in those crops.

Compounds which may be used as selective herbicides in oil-seed rape, for example, include compounds 38 and 58 of Table I. Preferably these compounds are used as a post-emergence treatment, that is to say, they are preferably applied after the crop has emerged from the soil. Rates of application are preferably from 1 to 4 kilograms per hectare.

Compounds which may be used as selective herbicides in maize include compounds 7 and 18 of Table I. Preferably the compounds are used in pre-emergence treatments at rates of 1 to 4 kilograms per hectare.

Compounds which may be used as selective herbicides in soyabean include compounds no 7, 50, and 51. Compounds 50 and 51 are preferably applied as pre-emergence treatments and compound 51 as a post-emergence treatment. Rates of application are preferably from 1 to 4 kilograms per hectare.

Compounds which may be used as selective herbicides in rice include compound no 18 of Table I. Preferably compound 18 is applied as a pre-emergence treatment at 1 to 4 kilograms per hectare. Compound no. 18 may also be used as a selective herbicide in sorghum and barley crops.

The compounds used in the process of the invention are preferably applied in the form of a composition, in which the active ingredient is mixed with a diluent or carrier. In another aspect, therefore, the invention provides a herbicidal composition, comprising as an active ingredient a compound of formula (I) as hereinbefore defined, in admixture with a solid or liquid diluent. Preferably the composition also comprises a surface-active agent.

The solid compositions of the invention may be for example, in the form of dusting powders, or may take the form of granules. Suitable solid diluents include, for example, kaolin, bentonite, kieselguhr, dolomite, calcium carbonate, talc, powdered magnesia, and Fuller's earth.

Solid compositions may also be in the form of dispersible powders or grains comprising in addition to the active ingredient, a wetting agent to facilitate the dispersion of the powder or grains in liquids. Such powders or grains may include fillers, suspending agents and the like.

Liquid compositions include aqueous solutions, dispersions and emulsions containing the active ingredient preferably in the presence of one or more surface active agents. Water or organic liquids may be used to prepare solutions, dispersions, or emulsions of the active ingredient. The liquid compositions of the invention may also contain one or more corrosion inhibitors for example lauryl isoquinolinium bromide.

Surface active agents may be of the cationic, anionic or non-ionic type. Suitable agents of the cationic type include for example quaternary ammonium compounds, for example cetyltrimethyl ammonium bromide. Suitable agents of the anionic type include for example soaps, salts of aliphatic mono-esters of sulphuric acid, for example sodium lauryl sulphate; and salts of sulphonated aromatic compounds, for example dodecylbenzenesulphonate, sodium, calcium and ammonium lignosulphonate, butylnaphthalene sulphonate, and a mixture of the sodium salts of diisopropyl- and triisopropyl-naphthalenesulphonic acid. Suitable agents of the non-ionic type include, for example, the condensation products of ethylene oxide with fatty alcohols such as oleyl alcohol and cetyl alcohol, or with alkyl phenols such as octyl-phenol, nonylphenol, and octylcresol. Other non-ionic agents are the partial esters derived from long chain fatty acids and hexitol anhydrides, for example sorbitol monolaurate; the condensation products of the said partial esters with ethylene oxide and the lecithins.

The compositions which are to be used in the form of aqueous solutions, dispersions or emulsions are generally supplied in the form of a concentrate containing a high proportion of the active ingredient, the concentrate being diluted with water before use. These concentrates are usually required to withstand storage for prolonged periods and after such storage to be capable of dilution with water in order to form aqueous preparations which remain homogeneous for a sufficient time to enable them to be applied by conventional spray equipment. In general concentrates may conveniently contain from 10 to 85% and preferably from 25 to 60% by weight of active ingredient. Dilute preparations ready for use may contain varying amounts of the active ingredient, depending upon the purpose for which they are to be used; however, dilute preparations suitable for many uses contain between 0.01% and 10% and preferably between 0.1% and 1% by weight of the active ingredient.

In another aspect, the invention provides processes for preparing compounds of the formula:

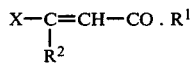

wherein X, $R^1$ and $R^2$ have the meanings previously assigned to them in this specification.

A suitable reaction scheme is as follows. Imidazole or 1,2,4-triazole is treated with a base to form an anion and the latter is then reacted with an α, β-dihalogeno ketone to give the required compounds. The halogen in the α, β-dihalogeno ketone is preferably bromine or chlorine.

The first stage of the reaction, in which the imidazole or 1,2,4-triazole is treated with a base, is preferably carried out in a diluent. Suitable diluents include aprotic solvents, for example hydrocarbons and ethers, and in particular dimethylformamide. Conveniently the base employed to form the anion is an alkali metal hydride, for example sodium hydride. The formation of the anion by treatment with base is preferably carried out at room temperature or below. The reaction mixture containing the anion may conveniently be used directly in the subsequent reaction. The subsequent reaction with the α, β-dihalogeno ketone is preferably carried out at a higher temperature, for example at 100° to 120° C. The product may be isolated by conventional methods, for example by pouring the reaction mixture into water, extracting with an organic solvent, evaporating the extracts, and purifying the residue by conventional methods, for example by recrystallisation. The solvent for the reaction with the dihalogenoketone may conveniently be the one in which the anion was prepared.

The dihalogeno ketones required as starting materials are known compounds or may be prepared by processes known in themselves, for example by addition of bromine or chlorine to suitable unsaturated ketones.

In a further aspect the present invention provides compounds of formula (I) whenever prepared by the processes herein described.

The invention is illustrated by the following Examples, in which all parts are by weight and all temperatures in degrees Centigrade unless otherwise stated.

EXAMPLE 1

This Example illustrates the preparation of compound no. 3 of Table I. 1,2,4-Triazole (4.64 g) in dry dimethylformamide (10 ml) was added slowly to a suspension of sodium hydride (2.88 g of 50% dispersion in mineral oil, washed free of oil with dry petrol) in dry dimethylformamide (10 ml) with cooling and stirring. A solution of 1-benzoyl-1,2-dibromo-2-(o-chlorophenyl) ethane (8.45 g) in dry dimethylformamide (10 ml) was then added and the mixture heated at 100° C. for 1 hour. The mixture was poured into cold water (1 liter) and extracted with ether. The ether extracts were dried and evaporated to give a yellow oil. This was dissolved in hexane and the solution cooled to $-15°$ C. The light yellow fibrous crystals were filtered off to give 1-benzoyl-2-o-chlorophenyl-2-(1,2,4-triazol-1-yl)-ethylene (compound no. 3 of Table I) having a melting point of 79°–81° C.

EXAMPLE 2

This Example illustrates the preparation of compound no. 2 of Table I).

1,2,4-Triazole (1.5 g) in dry dimethylformamide (5 ml) was added slowly to a suspension of sodium hydride (1.04 g of 50% suspension in oil, washed free of oil with dry petrol) in dry dimethyl formamide with cooling and stirring. A solution of 1-o-chlorophenyl-2,3-dibromo-3-pivaloyl ethane (2.8 g) in dry dimethylformamide (5.0 ml) was added and the mixture heated at 100° C. for 1 hour. The mixture was poured into cold water (500 ml) and the mixture extracted with ether. The ether extracts were dried and evaporated to give a pale yellow oil. The oil was dissolved in hexane and cooled to $-15°$ C. The yellow needles of 1-o-chlorophenyl-1-(1,2,4-triazol-1-yl)-2-pivaloylethylene (compounding no. 2 of Table I) were collected and had a melting point of 53°–55° C.

EXAMPLE 3

This Example illustrates the preparation of compound no. 1 of Table I.

2,2-Dimethyl-5-phenylpent-4-ene-3-one (9.48 g) in carbon tetrachloride (60 ml) was treated dropwise with bromine (8.0 g). The solution was evaporated in a vacuum and the pale yellow residue of 4,5-dibromo-2,2-dimethyl-5-phenylpentan-3-one (12.6 g) collected. The dibromo compound so prepared (6.96 g) was dissolved in dry dimethylformamide (20 ml) and added dropwise to a mixture obtained by adding 1,2,4-triazole (2.76 g) to a suspension of sodium hydride (1.92 of 50% dispersion in mineral oil, washed free of oil with dry petrol) in dimethylformamide (10 ml). The resulting mixture was heated on a steambath for 15 minutes and poured into cold water (200 ml). The mixture was extracted with ether and the ether extracts dried and evaporated to give a pale yellow oil. This oil crystallised from petrol to give 2,2-dimethyl-5-phenyl-5-(1,2,4-triazol-1-yl)pent-4-en-3-one (compound no. 1 of Table I) having a melting point of 70°–73° C.

EXAMPLE 4

This Example illustrates the preparation of compound no. 6 of Table I.

A solution of sodium hydroxide (20 g) in water (100 ml) was added dropwise with stirring to a solution of 2-methoxybenzaldehyde (65 g) and 2,2-dimethyl-butan-3-one (50 g) in ethanol (100 ml). The mixture was stirred at room temperature for 16 hours and then extracted with ether (200 ml, then 2×100 ml). The ether extracts were washed with dilute hydrochloric acid (100 ml) and then water (3×100 ml), dried over magnesium sulphate and evaporated under reduced pressure to a yellow oil. This oil was distilled and the distillate boiling at 105°–115° C./0.2 Torr collected. In an alternative purification step, the oil was dissolved in petroleum (500 ml) (b.p. 40°–60° C.) and kept at −10° C. for several days. The product separated as a crystalline solid of melting point 34°–36° C.

The unsaturated ketone so prepared (31.2 g) was heated under reflux in carbon tetrachloride (180 ml) with stirring while bromine (24.0 g) was added dropwise at such a rate that the solution remained almost colourless throughout the addition. The resulting solution was cooled to room temperature and evaporated under reduced pressure. The off-white solid remaining was recrystallised from hexane (500 ml) containing chloroform (10 ml) to give the alpha-beta-dibromo compound with a melting point of 116°–118° C.

A solution of 1,2,4-triazole (8.28 g) in dry dimethylformamide (35 ml) was added slowly to a suspension of sodium hydride (5.76 g of 50% dispersion in mineral oil washed free of oil with hexane) in dry dimethylformamide (25 ml) with stirring. A solution of the alpha-beta-dibromo compound prepared above (14.74 g) in dry dimethylformamide (40 ml) was then added dropwise and the mixture subsequently heated to 100° C. for 1 hour. The mixture was allowed to cool to room temperature and poured into cold water (500 ml) and extracted with ether (100 ml, then 2×50 ml). The ether extracts were washed with water (3×100 ml) dried with magnesium sulphate, and evaporated to give a yellow oil (11.7 g). This was dissolved in hexane and stored at −10° C. overnight. The yellow solid which separated was identified as compound no. 6 of Table I, with a melting point of 80°–85° C.

The p-toluenesulphonate salt of compound no. 6 was prepared as follows. Toluene-4-sulphonic acid monohydrate (4.2 g) and toluene (30 ml) were heated under reflux in a Dean and Stark apparatus until all the water had been removed azeotropically. The compound no. 6 prepared above was mixed with the toluene solution to give a yellow solution which crystallised as it cooled. The solid was collected and washed with petroleum (b.p. 40°–60° C.) to give the p-toluene sulphonate salt of compound no. 6. This was recrystallised from ethanol to give a product melting at 162°–163° C. The free compound no. 6 was regenerated by adding ethanol (5 ml) to the p-toluene sulphonate salt, followed by water (45 ml) and concentrated ammonia (5 ml). The suspension was stirred for 15 minutes and filtered to give purified compound no. 6, having a melting point of 95.5°–96.5° C.

EXAMPLE 5

This Example illustrates the preparation of compound no. 57 of Table I.

Imidazole (10.2 g) in dry dimethylformamide (40 ml) was added with stirring to a suspension of sodium hydride (6.9 g of 50% dispersion in mineral oil, washed free of oil with hexane) in dry dimethylformamide. A solution of 1,2-dibromo-4,4-dimethyl-1-(2-methylphenyl)-pentan-3-one (18.1 g) in dry dimethylformamide was then added dropwise and the mixture heated to 100° C. for 1 hour. The reaction mixture was allowed to cool to room temperature and poured into cold water (600 ml). The off-white solid was collected, dried, and recrystallised from the petroleum (b.p. 80°–100° C.) to give compound no. 57 with a melting point of 87°–88° C.

EXAMPLE 6

This Example illustrates the preparation of a metal complex according to the invention. A hot solution of zinc chloride (0.068 g) in ethanol (4 ml) was added to a solution of compound no. 29 of Table I (0.275 g) in hot ethanol (5 ml). The resulting solution was stirred for 15 minutes and the yellow zinc complex filtered off and dried. The complex had a melting point of 189°–191° C. The elemental analysis indicated a complex containing 2 moles of compound no. 29 to one mole of zinc chloride.

EXAMPLE 7

This Example illustrates the preparation of compound no. 117 of Table I.

A slow stream of chlorine was passed through a solution of 2,2-dimethyl-5-(3-methoxyphenyl)pent-4-en-3-one (10 g) in chloroform (50 ml) with stirring and cooling below 10° C. The resulting solution was evaporated under reduced pressure to give an oil which on storage gave a white solid. This was washed with petroleum (b.p. 30°–40° C.) to give 1,2-dichloro-4,4-dimethyl-1-(2-chloro-5-methoxyphenyl)-pentan-3-one having a melting point of 94°–98° C. This dichloro compound was reacted with 1,2,4-triazole treated with sodium hydride in dry dimethylformamide in the manner described in the previous Examples to give compound no. 117.

EXAMPLE 8

This Example illustrates the preparation of compound no. 125 of Table I.

Pinacolone (11 g) was added to a solution of sodium (2.3 g) in ethanol (50 ml). 2(2-Chloroethyl)-benzaldehyde (16.8 g) was then added and the mixture heated under reflux for 3 hours. The solvent was removed and the residue shaken with ether and water. The ether solution was evaporated to give an oil which was distilled at 118°–120° C./0.05 Torr. The distillate crystallised on standing and had a melting-point of 27°–30° C. This material was identified as 5-(2-vinylphenyl)-2,2-dimethyl-pent-4-en-3-one.

The above penten-3-one derivative (5.03 g) was dissolved in carbon tetrachloride (25 ml) and a solution of bromine (8 g) in carbon tetrachloride added dropwise with stirring. At the end of the addition the mixture was left for 30 minutes and the solvent then removed. The residue was recrystallised from petroleum to give the tetra-bromo compound of formula:

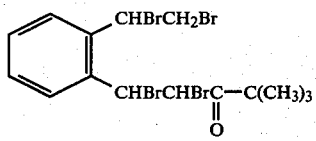

The tetrabromo compound so prepared (5.34 g) in dry dimethyl formamide (10 ml) was added to a solution prepared by adding sodium hydride (1.2 g) to dry dimethyl formamide, mixing a solution of triazole (3.45 g) in dimethyl-formamide (20 ml) therewith, leaving the mixture for 25 minutes and cooling the mixture to 0° C. The mixture was allowed to warm to room temperature and then heated on the steambath for 12 hours.

The mixture was cooled, poured into water, and extracted with three portions of ether. The ether extracts were washed with water, dried, and evaporated to give an oil. The oil was dissolved in petroleum (b.p. 30°–40° C.) and cooled in a refrigerator. The product (compound no. 125) separated as pale yellow crystals having a melting point of 129°–132° C.

EXAMPLE 9

This Example illustrates the preparation of compound no. 20. A solution of 1,2,4-triazole (0.69 g) in dry dimethylformamide (5 ml) was added dropwise to a suspension of sodium hydride (0.24 g) in dry dimethylformamide (5 ml). The solution was warmed until effervescence ceased and then cooled to room temperature. A solution of 5-chloro-2-methyl-5-phenylpent-4-en-3-one (2.08 g) in dry dimethylformamide (5 ml) was then added and the mixture stirred overnight. The suspension was poured into water, and extracted with ether. The ether extracts were washed with water, dried, and evaporated to give a yellow oil. This was taken up in hot toluene and added to a solution of p-toluenesulfphonic acid (1.18 g) in toluene (50 ml) and ethanol (5 ml). Some of the solvent was distilled off and the remaining solution cooled. The yellow solid which separated was recrystallised from a mixture of chloroform and hexane to yield one p-toluene-sulphonate salt (compound no. 20) as white crystals.

EXAMPLE 10

This Example illustrates the preparation of compound no. 99 of Table I.

A solution of 5-(2-carboxymethoxyphenyl)-2,2-dimethylpent-4-en-3-one (32.82 g) in dry ether (150 ml) mixed with chloroform (37.5 ml) was treated dropwise with bromine (6.47 ml) at 0° C. with stirring. Thirty minutes after addition was complete, the solvent was removed and the residue recrystallised from toluene/hexane to give the dibromo derivative, with a melting point of 165°–166° C.

Sodium hydride (4.8 g) in dry dimethylformamide (40 ml) was treated with 1,2,4-triazole (13.8 g) in dry dimethylformamide (30 ml) dropwise with stirring at room temperature. When effervescence had ceased, the dibromo compound prepared above (20.0 g) was added in solution in dry dimethylformamide (30 ml) and the mixture heated at 100° C. for 3 hours. The solution was cooled and about two thirds of the solvent removed. Water (25 ml) was added and the aqueous solution was washed with ether and then acidified with 2 M hydrochloric acid. The acidified solution was extracted with ether and the extracts dried and evaporated to give a white solid. This was recrystallised from a mixture of chloroform and petroleum (b.p. 60°–80° C.) to give compound no. 99.

The methyl ester (compound no. 135) of compound no. 99 was prepared by esterification of compound no. 99 with methanol and sulphuric acid in the conventional way for methyl esters.

EXAMPLE 11

This Example describes the preparation of 2,2-dimethyl-3-oxo-6-ethyl-4-octene, required as an intermediate for the preparation of compound no. 65 of Table I.

Dimethyl 3,3-dimethyl-2-oxobutylphosphonate (4 g) was dissolved in dry tetrahydrofuran (40 ml) and an equimolar amount of sodium hydride was added. The mixture was stirred for about 30 minutes and an equimolar amount of 2-ethylbutryaldehyde added. The mixture was heated under reflux for 6 hours, and then poured into water. The aqueous solution was extracted with dichloromethane and the extracts washed with brine, dried over magnesium sulphate, and evaporated to give the required compound as an almost colourless oil. This was used without further purification to prepare compound no. 65, following the procedure described in Example 3 for the preparation of compound no. 5 of Table I.

EXAMPLE 12

This Example illustrates the herbicidal properties of the compounds used in the process of the invention. Each compound (0.12 g) was formulated for test by mixing it with 5 ml of an emulsion prepared by diluting 100 ml of a solution containing 21.8 grams per liter of Span 80 and 78.2 grams per liter of Tween 20 in methyl cyclohexanone to 500 ml with water. Span 80 is a Trade Mark for a surface-active agent comprising sorbitan monolaurate. Tween 20 is a Trade Mark for a surface-active agent comprising a condensate of twenty molar porportions of ethylene oxide with sorbitan mono-oleate. The mixture of the compound and the emulsion was shaken with glass beads and diluted to 12 ml with water.

The spray composition so prepared was sprayed on to young pot plants (post-emergence test) of the species named in Table 2 below, at a rate equivalent to 1000 liters per hectare (10 kilograms of test compound per hectare). Damage to plants was assessed 14 days after spraying by comparison with untreated plants, on a scale of 0 to 3 where 0 is no effect and 3 represents 75 to 100% kill. In a test for pre-emergence herbicidal activity, seeds of the test species were placed on the surface of fibre trays of soil and were sprayed with the compositions at the rate of 1000 liters per hectare. The seeds were then covered with further soil. Three weeks after spraying, the seedlings in the sprayed fibre trays were compared with the seedlings in unsprayed control trays, the damage being assessed on the same scale of 0 to 3. The results are given in Tables 2 and 3 below:

TABLE 2

POST-EMERGENCE RESULTS

| COMPOUND NUMBER | LETTUCE | TOMATO | AVENA FATUA | LOLIUM PERENNE | CYPERUS ROTUNDUS | SETARIA VIRIDIS |
|---|---|---|---|---|---|---|
| 1 | 3 | 3 | 0 | 0 | 0 | |
| 2 | 3 | 3 | 0 | 1 | 0 | |
| 3 | 3 | 3 | 0 | 0 | 0 | 0 |
| 4 | 3 | 1 | 0 | 0 | 0 | 1 |
| 5 | 3 | 3 | 2 | 1 | 0 | 3 |
| 6 | 3 | 2 | 0 | 3 | 1 | 3 |
| 7 | 3 | 2 | 0 | 0 | 0 | 3 |
| 8 | 2 | 3 | 1 | 0 | 0 | 3 |
| 9 | 3 | 3 | 2 | 3 | 1 | 3 |
| 10 | 3 | 3 | 1 | 2 | 3 | 3 |
| 11 | 3 | 3 | 0 | 0 | 0 | 3 |
| 12 | 3 | 3 | 0 | 3 | 1 | 3 |
| 13 | 3 | 3 | 0 | 0 | 0 | 3 |
| 14 | 3 | 2 | 0 | 1 | 1 | 3 |
| 15 | 3 | 3 | 0 | 1 | 1 | 2 |
| 16 | 3 | 3 | 0 | 1 | 0 | 3 |
| 17 | 3 | 3 | 0 | 1 | 0 | 2 |
| 18 | 3 | 3 | 0 | 0 | 1 | 3 |
| 19 | 3 | 3 | 0 | 2 | 1 | 2 |
| 20 | 2 | 2 | 0 | 0 | 0 | 1 |
| 21 | 3 | 3 | 0 | 1 | 0 | 2 |
| 22 | 3 | 2 | 0 | 0 | 0 | 1 |
| 23 | 3 | 2 | 1 | 1 | 0 | 1 |
| 24 | 3 | 1 | 0 | 3 | 0 | 1 |
| 25 | 3 | 3 | 0 | 2 | 1 | 2 |
| 26 | 3 | 2 | 0 | 0 | 1 | 3 |
| 27 | 3 | 3 | 0 | 0 | 1 | 0 |
| 28 | 3 | 3 | 0 | 2 | 2 | 3 |
| 29 | 0 | 0 | 0 | 0 | 0 | 0 |
| 30 | 3 | 3 | 1 | 0 | 0 | 1 |
| 31 | 3 | 2 | 0 | 0 | 0 | 2 |
| 32 | 3 | 3 | 1 | 0 | 0 | 1 |
| 33 | 3 | 3 | 1 | 0 | 0 | 1 |
| 34 | 3 | 3 | 0 | 0 | 1 | 3 |
| 35 | 2 | 3 | 0 | 2 | 2 | 3 |
| 36 | 3 | 3 | 0 | 2 | 2 | 3 |
| 37 | 2 | 3 | 0 | 2 | 1 | 3 |
| 38 | 2 | 3 | 0 | 2 | 3 | 3 |
| 39 | 1 | 2 | 1 | 1 | 0 | 2 |
| 51 | 3 | 3 | 1 | 2 | 2 | 3 |
| 64 | 3 | 1 | 0 | 0 | 0 | 1 |
| 65 | 2 | 1 | 0 | 0 | 0 | 1 |

TABLE 3

PRE-EMERGENCE RESULTS

| COMPOUND NUMBER | LETTUCE | TOMATO | OAT | LOLIUM PERENNE | CYPERUS ROTUNDUS | SETARIA VIRIDIS |
|---|---|---|---|---|---|---|
| 1 | 3 | 2 | 2 | 3 | 3 | |
| 2 | 3 | 3 | 3 | 3 | 3 | 3 |
| 3 | 3 | 3 | 3 | 3 | 3 | 3 |
| 4 | 3 | 2 | 2 | 3 | 0 | 2 |
| 5 | 3 | 3 | 3 | 3 | 3 | 3 |
| 6 | 3 | 3 | 3 | 3 | 3 | 3 |
| 7 | | 3 | 3 | 3 | 0 | 3 |
| 8 | | 3 | 3 | 3 | 2 | 3 |
| 9 | | 3 | 3 | 3 | 3 | 3 |
| 10 | 3 | 3 | 3 | 3 | | 3 |
| 11 | 3 | 3 | 3 | 3 | 3 | 3 |
| 12 | 3 | 3 | 3 | 3 | | 3 |
| 13 | 3 | 3 | 0 | 3 | 0 | 3 |
| 14 | 3 | 3 | 0 | 1 | | |
| 15 | 3 | 3 | 2 | 3 | | 3 |
| 16 | 3 | 3 | 3 | 3 | | 3 |
| 17 | 2 | 3 | 3 | 3 | 0 | 3 |
| 18 | 3 | 3 | 3 | 3 | | 3 |
| 19 | 3 | 3 | 3 | 3 | 3 | 3 |
| 20 | 3 | 3 | 3 | 3 | 3 | 3 |
| 21 | 3 | 3 | 3 | 3 | 3 | 3 |
| 22 | 3 | 3 | 2 | 3 | 3 | 2 |
| 23 | 3 | 3 | 3 | 3 | 3 | 3 |
| 24 | 3 | 3 | 3 | 3 | 1 | 3 |
| 25 | 3 | 3 | 3 | 3 | 3 | 3 |
| 26 | 3 | 3 | 3 | 3 | 3 | 3 |
| 27 | 3 | 3 | 2 | 3 | 3 | 3 |
| 28 | 3 | 3 | 3 | 3 | 3 | 3 |
| 29 | 2 | 2 | 0 | 1 | 0 | 3 |
| 30 | 3 | 3 | 3 | 3 | 3 | 3 |
| 31 | 3 | 2 | 3 | 3 | 3 | 3 |
| 32 | 3 | 2 | 3 | 2 | 3 | 3 |
| 33 | 3 | 3 | 1 | 3 | 3 | 2 |
| 34 | 2 | 3 | 1 | 3 | 3 | 3 |
| 35 | 3 | 3 | 3 | 3 | 3 | 3 |
| 36 | 3 | 3 | 3 | 3 | 3 | 3 |
| 37 | 3 | 3 | 3 | 3 | 3 | 3 |
| 38 | 3 | 3 | 3 | 3 | 3 | 3 |
| 39 | 3 | 3 | 3 | 3 | 3 | 3 |
| 42 | 2 | 3 | 2 | 3 | 2 | 3 |
| 43 | 2 | 1 | 3 | 3 | 1 | 3 |
| 51 | 3 | 3 | 3 | 3 | 3 | 3 |
| 64 | 3 | 2 | 1 | 1 | 2 | 1 |
| 65 | 3 | 3 | 3 | 3 | 1 | 3 |

The names of the test plants are as follows:

| Le | Lettuce |
|---|---|
| To | Tomato |
| Ot/Av | Cultivated oats and wild oats (*Avena fatua*). Wild oats are used in the post-emergence test and cultivated oats in the pre-emergence test. |
| Dg | *Digitaria sanguinalis* |
| Ll | *Lolium perenne* (perennial rye grass) |
| Cn | *Cyperus rotundus* |

EXAMPLE 13

This Example illustrates the herbicidal properties of compounds used in the invention in relation to a wider range of test plants than in Example 12. Tests were carried out in a similar way to those of Example 12, but using a lower application rate. The compounds were formulated by mixing the appropriate ammount of each compound with 5 ml of an emulsion prepared by diluting 160 ml of a solution containing 21.8 grams per liter of Span 80 and 78.2 grams per liter of Tween 20 in methylcyclohexanone to 500 ml with water. The mixture of the compound and the emulsion was shaken with glass beads and diluted to 40 ml with water. Damage to plants was assessed on a scale of 0 to 5 where 0 is 0 to 20% damage and 5 is complete kill. In the table of results, if no result is given, this means that no test was made. The results are given in Tables 4 and 5 below.

TABLE 4

POST-EMERGENCE RESULTS

| COMPOUND NUMBER | SB | RP | CT | SY | MZ | WW | RC | SN | IP | AM | PI | CA |
|---|---|---|---|---|---|---|---|---|---|---|---|---|
| 40 | 1 | 1 | 1 | 2 | 3 | 3 | 1 | 3 | 3 | 3 | 2 | 3 |
| 41 | 0 | 1 | 1 | 2 | 2 | 2 | 2 | 2 | 3 | 3 | 0 | 3 |
| 45 | 1 | 1 | 0 | 2 | 0 | 0 | 0 | 2 | 2 | 3 | 0 | 3 |
| 46 | 3 | 1 | 2 | 4 | 4 | 3 | 2 | 3 | 2 | 4 | 3 | 3 |
| 47 | 3 | 3 | 2 | 4 | 4 | 4 | 2 | 4 | 3 | 4 | 3 | 4 |
| 48 | 1 | 3 | 2 | 4 | 1 | 4 | 1 | 3 | 3 | 4 | 3 | 4 |
| 49 | 3 | 3 | 1 | 3 | 1 | 4 | 1 | 3 | 2 | 3 | 2 | 4 |
| 50 | 2 | 3 | 1 | 4 | 3 | 4 | 3 | 4 | 3 | 4 | 3 | 4 |
| 52 | 1 | 1 | 0 | 2 | 0 | 0 | 0 | 1 | 1 | 0 | 0 | 0 |
| 53 | 2 | 1 | 1 | 2 | 2 | 4 | 2 | 3 | 3 | 3 | 3 | 2 |
| 54 | 2 | 3 | 3 | 3 | 0 | 4 | 1 | 4 | 4 | 4 | 4 | 2 |
| 55 | 2 | 3 | 2 | 2 | 4 | 4 | 0 | 4 | 4 | 4 | 3 | 3 |
| 56 | 0 | 2 | 2 | 3 | 3 | 4 | 0 | 2 | 4 | 4 | 3 | 3 |
| 57 | 1 | 4 | 4 | 4 | 1 | 4 | 0 | 3 | 4 | 4 | 4 | 3 |
| 58 | 0 | 1 | 1 | 4 | 0 | 3 | 0 | 3 | 3 | 4 | 3 | 3 |
| 59 | 1 | 1 | 1 | 4 | 0 | 0 | 0 | 3 | 3 | 2 | 2 | 2 |
| 60 | 2 | 3 | 2 | 4 | 0 | 3 | 1 | 3 | 4 | 3 | 2 | 4 |
| 61 | 0 | 0 | 0 | 1 | 0 | 0 | 0 | 0 | 3 | 0 | 0 | 1 |
| 62 | 2 | 2 | 1 | 3 | 0 | 0 | 0 | 2 | 2 | 3 | 2 | 4 |
| 66 | 2 | 1 | 2 | 4 | 4 | 4 | 0 | 4 | 4 | 4 | 4 | 4 |
| 67 | 2 | 2 | 2 | 4 | 4 | 3 | 1 | 4 | 4 | 4 | 3 | 2 |
| 68 | 0 | 1 | 3 | 3 | 3 | 1 | 0 | 0 | 4 | 3 | 3 | 3 |
| 69 | 0 | 2 | 2 | 4 | 3 | 1 | 0 | 1 | 4 | 3 | 2 | 0 |
| 70 | 1 | 1 | 2 | 4 | 0 | 1 | 0 | 2 | 4 | 1 | 2 | 2 |
| 71 | 1 | 0 | 1 | 3 | 0 | 0 | 0 | 1 | 0 | 2 | 0 | 0 |
| 72 | 1 | 3 | 3 | 4 | 3 | 4 | 2 | 4 | 4 | 3 | 3 | 3 |
| 73 | 1 | 0 | 1 | 0 | 3 | 2 | 2 | 2 | 4 | 4 | 3 | 3 |
| 74 | 1 | 2 | 0 | 3 | 2 | 0 | 3 | 2 | 4 | 4 | 3 | 3 |
| 75 | 1 | 2 | 1 | 3 | 2 | 0 | 3 | 3 | 4 | 4 | 4 | 3 |
| 76 | 0 | 0 | 1 | 3 | 0 | 0 | 0 | 0 | 4 | 3 | 3 | 2 |
| 77 | 0 | 0 | 3 | 4 | 0 | 0 | 3 | 3 | 3 | 4 | 3 | 3 |
| 78 | 1 | 2 | 1 | 3 | 1 | 1 | 0 | 1 | 3 | 2 | 2 | 1 |
| 79 | 0 | 0 | 2 | 3 | 1 | 2 | 2 | 2 | 4 | 3 | 3 | 2 |
| 80 | 0 | 0 | 2 | 3 | 2 | 2 | 2 | 1 | 4 | 2 | 4 | 2 |
| 81 | 0 | 1 | 1 | 2 | 1 | 2 | 1 | 4 | 4 | 3 | 3 | 2 |
| 82 | 1 | 2 | 0 | 3 | 1 | 1 | 1 | 3 | 3 | 3 | 3 | 1 |
| 83 | 2 | 2 | 1 | 3 | 2 | 2 | 1 | 3 | 4 | 3 | 3 | 1 |
| 84 | 2 | 2 | 2 | 3 | 2 | 3 | 1 | 3 | 4 | 3 | 3 | 2 |
| 85 | 1 | 1 | 1 | 3 | 2 | 1 | 0 | 3 | 4 | 4 | 4 | 1 |
| 86 | 2 | 3 | 0 | 3 | 3 | 3 | 0 | 4 | 3 | 4 | 3 | 3 |
| 87 | 1 | 4 | 0 | 1 | 2 | 2 | 0 | 4 | 3 | 4 | 3 | 2 |
| 88 | 1 | 4 | 0 | 4 | 2 | 3 |   | 3 | 3 | 4 | 2 | 2 |
| 89 | 1 | 3 | 1 | 0 | 2 | 2 | 0 | 2 | 4 | 4 | 0 | 3 |
| 90 | 2 | 4 | 0 | 1 | 2 | 3 | 0 | 2 | 3 | 4 | 3 | 3 |
| 91 | 1 | 4 | 1 | 1 | 2 | 2 |   | 3 | 3 | 3 | 3 | 2 |
| 92 | 1 | 4 | 1 | 1 | 3 | 4 | 0 | 4 | 3 | 4 | 3 | 3 |
| 93 | 1 | 4 | 1 | 1 | 3 | 3 | 0 | 4 | 4 | 4 | 3 | 2 |
| 94 | 2 | 4 | 1 | 2 | 3 | 2 | 2 | 4 | 4 | 4 | 4 | 3 |
| 95 | 2 | 4 | 1 | 1 | 2 | 3 | 0 | 4 | 4 | 4 | 3 | 3 |
| 96 | 2 | 4 | 1 | 2 | 2 | 0 | 1 | 4 | 4 | 4 | 2 | 3 |
| 97 | 2 | 4 | 1 | 2 | 2 | 3 | 0 | 4 | 4 | 4 | 4 | 2 |
| 98 | 3 | 4 | 1 | 2 | 2 | 2 |   | 4 | 4 | 4 | 3 | 3 |

| COMPOUND NUMBER | PO | XA | AB | CV | AV | DG | PU | ST | EC | SH | AG | CN |
|---|---|---|---|---|---|---|---|---|---|---|---|---|
| 40 | 4 | 4 | 3 | 4 | 0 | 4 | 0 | 3 | 4 | 1 | 1 | 0 |
| 41 | 4 | 2 | 3 | 3 | 0 | 4 | 0 | 0 | 3 | 3 | 0 | 0 |
| 45 | 3 | 3 | 2 | 2 | 0 | 0 | 0 | 0 | 0 | 1 | 0 | 0 |
| 46 | 3 |   | 2 | 2 | 0 | 4 | 3 | 4 | 2 | 2 | 0 | 2 |
| 47 | 4 |   | 3 | 3 | 0 | 4 | 2 | 4 | 3 | 3 | 0 | 1 |
| 48 | 3 |   | 3 | 3 | 0 | 1 | 1 | 2 | 0 | 0 | 0 | 0 |
| 49 | 3 |   | 1 | 2 | 0 | 2 | 1 | 2 | 0 | 0 | 0 | 0 |
| 50 | 4 |   | 3 | 3 | 3 | 4 | 3 | 4 | 4 | 3 | 2 | 2 |
| 52 | 1 | 1 | 2 | 1 | 0 | 0 | 0 | 0 | 0 | 0 | 0 | 0 |
| 53 | 3 | 2 | 3 | 2 | 3 | 3 | 2 | 3 | 0 | 2 | 0 | 1 |
| 54 | 3 | 3 | 2 | 2 | 0 | 2 | 1 | 2 | 1 | 2 | 0 | 0 |
| 55 | 4 | 4 | 3 | 3 | 4 | 3 | 1 | 4 | 0 | 0 | 0 | 0 |
| 56 | 4 | 4 | 3 | 2 | 0 | 0 | 0 | 3 | 0 | 0 | 0 | 0 |
| 57 | 4 | 4 | 4 | 3 | 0 | 4 | 1 | 4 | 0 | 2 | 0 | 0 |
| 58 | 4 | 4 | 4 | 3 | 0 | 1 | 0 | 3 | 1 | 1 | 0 | 0 |
| 59 | 1 | 3 | 3 | 3 | 0 | 1 | 0 | 2 | 0 | 0 | 0 | 0 |
| 60 | 4 | 3 | 2 | 2 | 4 | 0 | 3 | 0 | 1 | 0 | 0 |   |
| 61 | 0 | 0 | 1 | 0 | 0 | 0 | 0 | 0 | 0 | 0 | 0 | 0 |
| 62 | 4 | 3 | 3 | 2 | 0 | 1 | 2 | 2 | 4 | 0 | 0 | 0 |
| 66 | 4 | 4 | 4 | 3 | 4 | 4 | 3 | 4 | 3 | 3 | 1 | 2 |
| 67 | 4 | 4 | 4 | 4 | 1 | 4 | 0 | 4 | 2 | 2 | 0 | 0 |
| 68 | 2 | 3 | 4 | 4 | 0 | 2 | 0 | 2 | 3 | 1 | 0 | 0 |
| 69 | 3 | 2 | 2 | 0 | 2 | 0 | 3 | 0 | 1 | 0 | 0 |   |

TABLE 4-continued

POST-EMERGENCE RESULTS

| | | | | | | | | | | | | |
|---|---|---|---|---|---|---|---|---|---|---|---|---|
| 70 | 2 | 2 | 4 | 4 | 0 | 1 | 0 | 1 | 1 | 1 | 0 | 0 |
| 71 | 0 | 0 | 1 | 0 | 0 | 0 | 0 | 0 | 0 | 0 | 0 | 0 |
| 72 | 3 | 3 | 4 | 2 | 1 | 1 | 0 | 3 | 2 | 1 | 0 | 0 |
| 73 | 3 | 4 | 4 | 3 | 2 | 3 | 2 | 4 | 1 | 1 | 0 | 3 |
| 74 | 3 | 4 | 4 | 3 | 2 | 1 | 2 | 2 | 2 | 2 | 0 | 1 |
| 75 | 4 | 4 | 3 | 4 | 2 | 2 | 2 | 2 | 0 | 4 | 0 | 0 |
| 76 | 3 | 3 | 3 | 3 | 0 | 0 | 0 | 1 | 0 | 0 | 0 | 0 |
| 77 | 3 | 4 | 3 | 3 | 0 | 2 | 0 | 2 | 0 | 0 | 0 | 0 |
| 78 | 3 | 4 | 2 | 3 | 1 | 3 | 1 | 0 | 1 | 1 | 2 | 0 |
| 79 | 4 | 4 | 3 | 2 | 0 | 4 | 2 | 2 | 2 | 1 | 1 | 3 |
| 80 | 4 | 4 | 4 | 3 | 1 | 4 | 2 | 3 | 3 | 4 | 1 | 3 |
| 81 | 4 | 4 | 3 | 2 | 0 | 3 | 2 | 1 | 0 | 2 | 1 | 3 |
| 82 | 4 | 4 | 2 | 3 | 0 | 3 | 3 | 1 | 0 | 2 | 3 | 1 |
| 83 | 4 | 4 | 3 | 2 | 0 | 3 | 1 | 2 | 3 | 3 | 2 | 0 |
| 84 | 4 | 4 | 3 | 3 | 0 | 4 | 2 | 0 | 2 | 4 | 3 | 0 |
| 85 | 4 | 4 | 3 | 3 | 0 | 2 | 2 | 2 | 1 | 2 | 2 | 0 |
| 86 | 4 | 4 | 4 | 3 | 0 | 3 | 2 | 1 | 3 | | 0 | 0 |
| 87 | 4 | 4 | 4 | 3 | 0 | 3 | 3 | 3 | 3 | | 0 | 1 |
| 88 | 4 | 4 | 3 | 4 | 0 | 2 | 2 | 1 | 4 | | 0 | 0 |
| 89 | 3 | 3 | 2 | 0 | 0 | 0 | 0 | 0 | 2 | | 0 | 0 |
| 90 | 4 | 4 | 4 | 4 | 0 | 3 | 1 | 3 | 2 | | 0 | 0 |
| 91 | 4 | 3 | 3 | 4 | 0 | 2 | 1 | 1 | 2 | | 0 | 0 |
| 92 | 4 | 4 | 3 | 2 | 0 | 4 | 3 | 3 | 4 | | 2 | 1 |
| 93 | 4 | 4 | 4 | 4 | 1 | 4 | 3 | 3 | 4 | | 1 | 0 |
| 94 | 4 | 4 | 3 | 3 | 1 | 4 | 3 | 4 | 4 | | 2 | 1 |
| 95 | 4 | 4 | 3 | 4 | 1 | 4 | 1 | 2 | 4 | | 2 | 0 |
| 96 | 4 | 4 | 4 | 4 | 0 | 4 | 1 | 0 | 4 | | 0 | 0 |
| 97 | 4 | 4 | 4 | 4 | 0 | 4 | 2 | 1 | 4 | | 0 | 0 |
| 98 | 4 | 4 | 4 | 4 | 1 | 3 | 2 | 2 | 4 | | 1 | 0 |

TABLE 5

PRE-EMERGENCE RESULTS

| COMPOUND NUMBER | SB | RP | CT | SY | MZ | WW | RC | SN | IP | AM | PI | CA |
|---|---|---|---|---|---|---|---|---|---|---|---|---|
| 40 | 4 | 4 | 4 | 4 | 5 | 5 | 5 | 4 | 4 | 4 | 4 | 4 |
| 41 | 4 | 4 | 4 | 4 | 4 | 4 | 4 | 4 | 4 | 4 | 4 | 4 |
| 45 | 4 | 4 | 3 | 4 | 0 | 2 | 4 | 4 | 4 | 4 | 4 | 4 |
| 46 | 3 | 3 | 2 | 1 | 2 | 4 | 4 | 4 | 3 | 4 | 3 | 0 |
| 47 | 4 | 3 | 3 | 4 | 3 | 4 | 4 | 4 | 3 | 4 | 4 | 4 |
| 48 | 3 | 3 | 3 | 3 | 0 | 4 | 1 | 4 | 1 | 4 | 4 | 4 |
| 49 | 4 | 2 | 2 | 1 | 0 | 1 | 1 | 3 | 3 | 4 | 3 | 3 |
| 50 | 4 | 3 | 3 | 3 | 3 | 4 | 4 | 4 | 4 | 4 | 4 | 3 |
| 52 | 1 | 2 | | 2 | 1 | 4 | 4 | 4 | 1 | 2 | 1 | 2 |
| 53 | 3 | 2 | 4 | 4 | 4 | 4 | 5 | 4 | 3 | 4 | 4 | 3 |
| 54 | 4 | 4 | 0 | 1 | 1 | 4 | 4 | 4 | 3 | 4 | | 4 |
| 55 | 4 | 4 | 2 | 2 | 4 | 4 | 4 | 4 | 3 | 4 | | 3 |
| 56 | 4 | 4 | 1 | 0 | 0 | 4 | 4 | 4 | 2 | 4 | | 4 |
| 57 | 4 | 4 | | 3 | 4 | 4 | 4 | 4 | 3 | 4 | | 4 |
| 58 | 4 | 4 | | 4 | 4 | 4 | 4 | 4 | 4 | 4 | | 4 |
| 59 | 3 | 4 | 1 | 2 | 3 | 0 | 4 | 4 | 3 | 4 | | 4 |
| 60 | 4 | 4 | 0 | 1 | 0 | 4 | 4 | 4 | 4 | 5 | | 4 |
| 61 | 0 | 0 | 0 | 0 | 0 | 1 | 4 | 2 | 0 | 4 | | 2 |
| 62 | 4 | 4 | 1 | 4 | 4 | 4 | 4 | 3 | 3 | 4 | | 4 |
| 63 | 1 | 1 | | 1 | 0 | 3 | 0 | 3 | 0 | 4 | | 3 |
| 66 | 4 | 4 | 4 | 4 | 4 | 5 | 5 | 4 | 4 | 4 | | 4 |
| 67 | 4 | 4 | 1 | 3 | 2 | 4 | 4 | 4 | 3 | 4 | | 3 |
| 68 | 1 | 2 | 0 | 0 | 0 | 1 | 3 | 1 | 4 | 3 | | 2 |
| 69 | 4 | 1 | 0 | 1 | 0 | 2 | 3 | 4 | 0 | 4 | | 4 |
| 70 | 4 | 4 | | 3 | 0 | 2 | 2 | 4 | 3 | 4 | | 3 |
| 71 | 1 | 1 | 0 | 0 | 0 | 1 | 1 | 4 | 1 | 2 | | 2 |
| 72 | 4 | 4 | 1 | 2 | 0 | 4 | 4 | 4 | 2 | 4 | | 4 |
| 73 | 4 | 2 | 3 | 4 | 4 | 4 | 5 | | 4 | 4 | | 4 |
| 74 | 4 | 4 | 0 | 4 | 3 | 4 | 4 | | 3 | 4 | | 2 |
| 75 | 4 | 4 | 4 | 4 | 4 | 5 | 5 | | 4 | 4 | | 4 |
| 76 | 1 | 1 | 0 | 0 | 0 | 0 | 2 | | 2 | 4 | | 0 |
| 77 | 4 | 4 | 3 | 4 | 4 | 4 | 4 | | 2 | 4 | | 3 |
| 78 | 4 | 4 | 4 | 4 | 4 | 4 | 4 | | 3 | 4 | 4 | 4 |
| 79 | 4 | 4 | 4 | 4 | 4 | 4 | 5 | | 4 | 4 | 4 | 4 |
| 80 | 4 | 4 | 4 | 4 | 4 | 4 | 5 | | 4 | 4 | 4 | 4 |
| 81 | 4 | 4 | 4 | 4 | 4 | 4 | 5 | | 4 | 4 | 4 | 4 |
| 82 | 4 | 4 | 1 | 4 | 0 | 4 | 4 | | 0 | 4 | 4 | 4 |
| 83 | 4 | 4 | 3 | 3 | 2 | 4 | 4 | | 3 | 4 | 4 | 4 |
| 84 | 4 | 4 | 3 | 4 | 4 | 4 | 5 | | 4 | 4 | 4 | 4 |
| 85 | 4 | 3 | 0 | 2 | 0 | 4 | 4 | | 0 | 4 | 4 | 4 |
| 86 | 3 | 3 | 3 | 3 | 1 | 4 | 4 | | 2 | 3 | 2 | |
| 87 | 3 | 2 | 3 | 2 | 1 | 4 | 4 | | 3 | 3 | 3 | |
| 88 | 3 | 4 | 3 | 1 | 2 | 4 | 4 | | 3 | 4 | 3 | |
| 89 | 4 | 4 | 4 | 3 | 0 | 0 | 4 | | 4 | 2 | 3 | |

TABLE 5-continued

PRE-EMERGENCE RESULTS

| | | | | | | | | | | | |
|---|---|---|---|---|---|---|---|---|---|---|---|
| 90 | 4 | 4 | 3 | 3 | 3 | 4 | 4 | | 3 | 3 | |
| 91 | 4 | 4 | 2 | 2 | 1 | 2 | 2 | | 0 | 0 | 0 |
| 92 | 4 | 4 | 4 | 4 | 4 | 4 | 5 | | 4 | 3 | 4 |
| 93 | 3 | 4 | 4 | 4 | 4 | 4 | 5 | | 4 | 2 | 2 |
| 94 | 4 | 4 | 3 | 4 | 2 | 4 | 5 | | 4 | 4 | |
| 95 | 4 | 3 | 3 | 4 | 3 | 4 | 4 | | 4 | 4 | 3 |
| 96 | 4 | 4 | 4 | 4 | 3 | 3 | 5 | | 4 | 3 | 4 |
| 97 | 4 | 4 | 4 | 4 | 4 | 4 | 5 | | 4 | 4 | 4 |
| 98 | 4 | 4 | 3 | 4 | 1 | 4 | 5 | | 4 | | 4 |

| COMPOUND NUMBER | PO | XA | AB | CV | OT | DG | PU | ST | EC | SH | AG | CN |
|---|---|---|---|---|---|---|---|---|---|---|---|---|
| 40 | 4 | 4 | 4 | | 5 | 5 | 4 | 4 | 5 | 4 | 5 | 4 |
| 41 | 4 | 3 | 4 | | 4 | 4 | 4 | 4 | 5 | 4 | 2 | 5 |
| 45 | 4 | 2 | 4 | | 2 | 4 | 4 | 2 | 4 | 2 | 2 | 3 |
| 46 | 4 | 3 | 3 | | 4 | 4 | 4 | 4 | 5 | 4 | 3 | 2 |
| 47 | 4 | 3 | 3 | | 4 | 4 | 4 | 4 | 5 | 4 | 4 | 4 |
| 48 | 4 | 3 | 2 | | 0 | 4 | 4 | 4 | 4 | 4 | 0 | 0 |
| 49 | 3 | 1 | 2 | | 0 | 4 | 4 | 4 | 2 | 2 | 0 | 1 |
| 50 | 4 | 3 | 3 | | 4 | 4 | 4 | 4 | 4 | 4 | 4 | 4 |
| 52 | 2 | 1 | 1 | | 2 | 4 | 4 | 4 | 4 | 3 | 0 | 1 |
| 53 | 4 | 4 | 3 | | 5 | 4 | 4 | 4 | 5 | 4 | 4 | 5 |
| 54 | 4 | 3 | 4 | | 2 | | 4 | 4 | 4 | 3 | 3 | 2 |
| 55 | 4 | 2 | 4 | | 4 | | 4 | 4 | 4 | 4 | 3 | 4 |
| 56 | 4 | 4 | 2 | | 4 | | 4 | 4 | 5 | 3 | 3 | 1 |
| 57 | 4 | 3 | 4 | | 4 | | 4 | 4 | 5 | 4 | 4 | 0 |
| 58 | 4 | 4 | 4 | | 4 | | 4 | 4 | 5 | 4 | 4 | 2 |
| 59 | 4 | 2 | 4 | | 0 | | 3 | 4 | 4 | 2 | 2 | 3 |
| 60 | 4 | 3 | 5 | | 4 | | 4 | 4 | 1 | 4 | 0 | 0 |
| 61 | 3 | 0 | 1 | | 0 | | 1 | 0 | 1 | 0 | 0 | 0 |
| 62 | 4 | 1 | 4 | | 4 | | 4 | 5 | 5 | 4 | 4 | 4 |
| 63 | 4 | 0 | 3 | | 1 | | 1 | 4 | 5 | 0 | 4 | 0 |
| 66 | 4 | 4 | 4 | | 4 | | 4 | 4 | 5 | 4 | 5 | 5 |
| 67 | 4 | 3 | 4 | | 4 | | 4 | 5 | 5 | 4 | 4 | 0 |
| 68 | 3 | 0 | 0 | | 0 | | 4 | 4 | 4 | 0 | 0 | 0 |
| 69 | 4 | 0 | 0 | | 1 | | 4 | 4 | 2 | 0 | 0 | 1 |
| 70 | 4 | 0 | 2 | | 0 | | 1 | 3 | 4 | 2 | 0 | 0 |
| 71 | 3 | 1 | 0 | | 1 | | 0 | 0 | 2 | 0 | 0 | 1 |
| 72 | 4 | 0 | 4 | | 4 | | 4 | 4 | 5 | 1 | 0 | 0 |
| 73 | 4 | 2 | 4 | | 4 | | 5 | 4 | 4 | 4 | 4 | 1 |
| 74 | 4 | 0 | 4 | | 3 | | 5 | 4 | 5 | 4 | 3 | 1 |
| 75 | 4 | 4 | 5 | | 5 | | 5 | 5 | 5 | 4 | 4 | 5 |
| 76 | 4 | 0 | 4 | | 0 | | 4 | 4 | 4 | 2 | 4 | 0 |
| 77 | 4 | 3 | 4 | | 4 | | 4 | 4 | 5 | 4 | 4 | 4 |
| 78 | 4 | 3 | 4 | | 4 | | 4 | 4 | 4 | 4 | 3 | 2 |
| 79 | 4 | 4 | 4 | | 4 | | 4 | 4 | 5 | 4 | 4 | 4 |
| 80 | 4 | 4 | 4 | | 4 | | 4 | 4 | 5 | 4 | 4 | 5 |
| 81 | 4 | 4 | 4 | | 4 | | 4 | 4 | 4 | 4 | 4 | 4 |
| 82 | 4 | 3 | 4 | | 2 | | 4 | 4 | 4 | 4 | 2 | 2 |
| 83 | 4 | 4 | 4 | | 4 | | 4 | 4 | 5 | 4 | 3 | 4 |
| 84 | 4 | 3 | 4 | | 4 | | 4 | 4 | 5 | 4 | 4 | 4 |
| 85 | 4 | 3 | 4 | | 4 | | 4 | 4 | 5 | 4 | 2 | 1 |
| 86 | 4 | 4 | 3 | | 4 | | 4 | 4 | 5 | 4 | 3 | 0 |
| 87 | 3 | 4 | 3 | | 4 | | 4 | 4 | 4 | 4 | 1 | 0 |
| 88 | 3 | 4 | 4 | | 4 | | 4 | 4 | 5 | 4 | 4 | 1 |
| 89 | 3 | 4 | 3 | | 1 | | 2 | 4 | 2 | 2 | 3 | 5 |
| 90 | | 4 | 3 | | 4 | | 4 | 4 | 5 | 4 | 4 | 2 |
| 91 | 4 | 0 | 2 | | 0 | | 3 | 4 | 3 | 0 | 0 | 0 |
| 92 | | 4 | 4 | | 4 | | 5 | 4 | 4 | 4 | 4 | 5 |
| 93 | 2 | 4 | 3 | | 4 | | 4 | 4 | 5 | 4 | 4 | 5 |
| 94 | | 4 | 4 | | 4 | | 4 | 4 | 5 | 4 | 4 | 3 |
| 95 | | 4 | 3 | | 4 | | 4 | 4 | 4 | 4 | 4 | 5 |
| 96 | 3 | 4 | 4 | | 4 | | 4 | 4 | 4 | 4 | 4 | 5 |
| 97 | | 4 | 4 | | 4 | | 4 | 4 | 5 | 4 | 4 | 5 |
| 98 | | 4 | 4 | | 4 | | 4 | 4 | 5 | 4 | 4 | 2 |

| Names of test plants in Tables 4 and 5 | | Names of test plants in Tables 4 and 5 | |
|---|---|---|---|
| Sb | Sugar beet | Pi | Polygonum aviculare |
| Rp | Rape | Ca | Chenopodium album |
| Ct | Cotton | Po | Portulaca oleracea |
| Sy | Soya bean | Ab | Abutilon theophrastii |
| Mz | Maize | Cv | Convolvulus arvensis |
| Ww | Winter wheat | Ot/Av | As in Example 12 |
| Rc | Rice | Dg | Digitaria snaguinalis |
| Sn | Senecio vulgaris | Pu | Poa annua |
| Ip | Ipomoea purpurea | St | Setaria viridis |
| Am | Amaranthus retroflexus | Ec | Echinochloa crus-galli |

-continued

| Names of test plants in Tables 4 and 5 | |
| --- | --- |
| Sh | *Sorghum halepense* |
| Ag | *Agropyron repens* |
| Cp | *Cyperus rotundus* |

EXAMPLE 14

This Example illustrates selective herbicidal properties of certain compounds according to the invention. The compounds were formulated as described in Example 13 and tests were carried out as described in that Example, except that the pre-emergence test was performed slightly differently. The seeds of the test plants were sown in a shallow groove, the surface levelled and sprayed with the test compound, and the surface was then covered with a thin layer of soil. The results of the test were assessed 26 days after treatment, on a scale of 0 to 9 where 0 is 0 to 10% damage and 9 is 90 to 100% damage. Results are given in Table 6 below.

TABLE 6

| COM- POUND NO | RATE OF APPLI- CATION KG/HA | PRE-OR POST- EMER- GENCE APPLI- CATION | TEST PLANTS | | | | | | | | | | | | | | | | | |
| --- | --- | --- | --- | --- | --- | --- | --- | --- | --- | --- | --- | --- | --- | --- | --- | --- | --- | --- | --- | --- |
| | | | Mz | Rc | Sy | Ct | To | Sg | Am | Ip | Ab | Se | Si | Ds | Xa | Ec | Dg | St | Sh | Pm | Cd | Cn |
| 7 | 2 | Pre | 0 | 6 | 0 | 3 | 2 | 3 | 8 | 4 | 4 | 4 | 8 | 5 | 6 | 9 | 9 | 9 | 9 | 9 | — | 4 |
| 18 | 1 | Pre | 0 | 1 | 7 | 3 | 5 | 0 | 7 | 4 | 4 | 8 | 8 | 4 | 1 | 8 | 9 | 7 | 2 | 8 | — | 2 |

The names of the test plants are as follows:

| Mz | Maize |
| --- | --- |
| Rc | Rice |
| Sy | Soya bean |
| Ct | Cotton |
| To | Tomato |
| Sg | Sorghum |
| Am | *Amaranthus retroflexus* |
| Ip | *Ipomoea purpurea* |
| Ab | *Abutilon theophrasti* |
| Se | *Sesbania exaltata* |
| Si | *Sida spinosa* |
| Ds | *Daturia stramonium* |
| Xa | *Xanthium pensylvanicum* |
| Ec | *Echinochloa crus-galli* |
| Dg | *Digitaria sanguinalis* |
| St | *Setaria viridis* |
| Sh | *Sorghum halepense* |
| Pm | *Panicum maximum* |
| Cd | *Cyperus difformis* |
| Cn | *Cyperus rotundus* |

It will be seen from Table 6 that compound 7 leaves maize substantially undamaged at a rate of application which severely damages a variety of weed species. Similarly compound no 18 leaves both maize and sorghum substantially undamaged while severely affecting a number of weed species.

We claim:

1. A herbicidal compound of the formula:

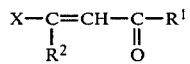

wherein X is a 1-(1,2,4-triazolyl) radical or a 1-imidazolyl radical; $R^2$ is an alkyl or cycloalkyl radical of 2 to 10 carbon atoms or a phenyl or naphthyl radical optionally bearing one or more substituents selected from the group consisting of fluorine, chlorine, bromine, iodine, cyano, nitro, alkyl of 1 to 6 carbon atoms, alkoxy of 1 to 6 carbon atoms optionally substituted by one or more phenyl radicals or alkoxy radicals of 1 to 6 carbon atoms; alkylthio of 1 to 6 carbon atoms; haloalkyl of 1 to 6 carbon atoms; haloalkoxy of 1 to 6 carbon atoms; carboxyalkoxy in which the alkoxy group has from 1 to 6 carbon atoms; alkoxycarbonylalkoxy in which each alkoxy group has from 1 to 6 carbon atoms; N,N-dialkylcarbamoylalkoxy in which the alkoxy group and each alkyl group each has from 1 to 6 carbon atoms; phenyl; or 1-(1,2,4-triazolyl)-vinyl; and $R^1$ is an alkyl or cycloalkyl radical of 2 to 10 carbon atoms, or a phenyl or naphthyl radical optionally bearing one or more of the substituents listed for $R^2$ above; or an acid addition salt or metal complex thereof.

2. A herbicidal compound according to claim 1, wherein the group $R^1$ is a tertiary butyl radical, X is a 1-(1,2,4-triazolyl) or 1-imidazolyl radical, and $R^2$ is a phenyl or 1-naphthyl radical optionally bearing one or more substituents selected from those defined for $R^2$ in claim 1.

3. A compound according to claim 1 wherein X is a 1-(1,2,4-triazolyl) or 1-imidazolyl group, $R^1$ is a phenyl group optionally bearing one or more substituents selected from the group consisting of fluorine, chlorine, bromine, iodine, alkyl of 1 to 6 carbon atoms, and alkoxy of 1 to 6 carbon atoms; and $R^2$ is a phenyl or 1-naphthyl radical optionally bearing one or more substituents selected from the group defined for $R^2$ in claim 1.

4. A process of killing or severely injuring unwanted plants, which comprises applying to the plants, or to the growth medium thereof, a compound of the formula:

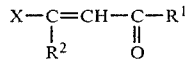

or an acid addition salt or metal complex thereof, wherein X is a 1-(1,2,4-triazolyl) radical or a 1-imidazolyl radical; $R^2$ is an alkyl or cycloalkyl radical of 2 to 10 carbon atoms or a phenyl or naphthyl radical optionally bearing one or more substituents selected from the group consisting of fluorine, chlorine, bromine, iodine, cyano, nitro, alkyl of 1 to 6 carbon atoms, alkoxy of 1 to 6 carbon atoms optionally substituted by one or more phenyl radicals or alkoxy radicals of 1 to 6 carbon atoms; alkylthio of 1 to 6 carbon atoms; haloalkyl of 1 to 6 carbon atoms; haloalkoxy of 1 to 6 carbon atoms; carboxyalkoxy in which the alkoxy group has from 1 to 6 carbon atoms; alkoxycarbonylalkoxy in which each alkoxy group has from 1 to 6 carbon atoms; N,N-dialkylcarbamoylalkoxy in which the alkoxy group and each alkyl group each has from 1 to 6 carbon atoms; phenyl; or 1-(1,2,4-triazolyl)-vinyl; and $R^1$ is an alkyl or cycloalkyl radical of 2 to 10 carbon atoms, or a phenyl or naphthyl radical optionally bearing one or more of the substituents listed for $R^2$ above; or an acid addition salt or metal complex thereof.

5. A process according to claim 4 wherein the rate of application of the compound is from 0.25 to 10.0 kilograms per hectare.

6. A herbicidal composition comprising as an active ingredient a herbicidally effective amount of a compound of the formula:

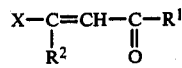

or an acid addition salt or metal complex thereof, wherein X, $R^1$, and $R^2$ are as defined in claim 1, in admixture with a carrier comprising a solid or liquid diluent.

7. A herbicidal composition according to claim 6 which further comprise a surface-active agent.

8. A process of preparing compounds of the formula (I)

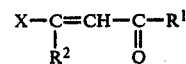

wherein X, $R^1$ and $R^2$ are as defined in claim 1, which comprises treating imidazole or 1,2,4-triazole with a base to provide the imidazole or 1,2,4-triazole anion and reacting an alpha, beta dihalogenoketone of the formula:

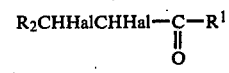

with said anion.

* * * * *